(12) United States Patent
Whitaker et al.

(10) Patent No.: US 9,750,419 B2
(45) Date of Patent: Sep. 5, 2017

(54) SYSTEMS AND METHODS FOR BLOOD PRESSURE MEASUREMENT

(71) Applicant: Welch Allyn, Inc., Skaneateles Falls, NY (US)

(72) Inventors: Tyson B. Whitaker, Arden, NC (US); David E. Quinn, Auburn, NY (US); Shawn C. St. Pierre, Skaneateles Falls, NY (US); Matthew J. Kinsley, Liverpool, NY (US); John A. Lane, Weedsport, NY (US); Joseph Buchanon, Skaneateles Falls, NY (US)

(73) Assignee: Welch Allyn, Inc., Skaneateles Falls, NY (US)

(*) Notice: Subject to any disclaimer, the term of this patent is extended or adjusted under 35 U.S.C. 154(b) by 750 days.

(21) Appl. No.: 14/183,074

(22) Filed: Feb. 18, 2014

(65) Prior Publication Data
US 2015/0230718 A1    Aug. 20, 2015

(51) Int. Cl.
*A61B 5/02* (2006.01)
*A61B 5/022* (2006.01)
*A61B 5/021* (2006.01)

(52) U.S. Cl.
CPC .......... *A61B 5/022* (2013.01); *A61B 5/02116* (2013.01); *A61B 5/02141* (2013.01)

(58) Field of Classification Search
USPC ................................ 600/480, 300, 485–500
See application file for complete search history.

(56) References Cited

U.S. PATENT DOCUMENTS 4,928,701 A     5/1990   Harada et al.
5,054,494 A *  10/1991   Lazzaro ............... A61B 5/7242
                                                           600/490

(Continued)

FOREIGN PATENT DOCUMENTS

EP          0585460          9/1994
WO     2010/150128 A1    12/2010

OTHER PUBLICATIONS

Gesche et al., "Continuous Blood Pressure Measurement by Using the Pulse Transit Time: Comparison to a Cuff-Based Method", European Journal of Applied Physiology, 2012, vol. 112, No. 1 (Jan.), pp. 309-315.

(Continued)

*Primary Examiner* — Michael Kahelin
*Assistant Examiner* — Mitchell E Alter
(74) *Attorney, Agent, or Firm* — Lee & Hayes, PLLC

(57) ABSTRACT

A method of determining a blood pressure of a patient includes determining a plurality of pressure pulses, wherein each pressure pulse of the plurality of pressure pulses comprises a profile having a maximum profile height. The method also includes determining a pulse score associated with the plurality of pressure pulses, wherein the pulse score is determined based on the profiles of the pressure pulses and the maximum profile heights. The method further includes determining that the pulse score is above a pulse score threshold, and generating, in response to determining that the pulse score is above the pulse score threshold, a pulse curve based on the maximum profile heights. The method also includes determining the blood pressure of the patient without completely occluding a blood vessel of the patient, wherein the blood pressure is determined based on a plurality of values corresponding to respective points on the pulse curve.

25 Claims, 7 Drawing Sheets

(56) References Cited

U.S. PATENT DOCUMENTS

| | | | |
|---|---|---|---|
| 5,178,152 A | 1/1993 | Ozawa | |
| 5,339,818 A * | 8/1994 | Baker | A61B 5/02156 128/925 |
| 5,542,428 A | 8/1996 | Jayne | |
| 5,785,659 A * | 7/1998 | Caro | A61B 5/02125 600/485 |
| 5,791,348 A * | 8/1998 | Aung | A61B 5/02116 600/493 |
| 5,853,005 A | 12/1998 | Scanlon | |
| 6,808,496 B2 | 10/2004 | Oka et al. | |
| 6,923,769 B2 | 8/2005 | Nishii et al. | |
| 7,018,337 B2 | 3/2006 | Hood, Jr. | |
| 7,941,199 B2 | 5/2011 | Kiani | |
| 8,016,765 B2 | 9/2011 | Ramsey | |
| 2002/0035332 A1 | 3/2002 | Chen et al. | |
| 2004/0181157 A1 | 9/2004 | Medero et al. | |
| 2005/0033188 A1 * | 2/2005 | Whitaker | A61B 5/02233 600/490 |
| 2007/0185401 A1 | 8/2007 | Quinn et al. | |
| 2008/0146947 A1 | 6/2008 | Kojima et al. | |
| 2011/0295126 A1 * | 12/2011 | Quinn | A61B 5/02225 600/481 |
| 2012/0059267 A1 | 3/2012 | Lamego et al. | |
| 2012/0149994 A1 * | 6/2012 | Luczyk | A61B 5/02225 600/301 |

OTHER PUBLICATIONS

Jilek et al., "The Contours of Arterial Pulsations in the Blood Pressure Cuff are Hemodynamic Waveforms rather than Oscillations", Proceedings of the $2^{nd}$ International Conference on Circuits, Systems, Control, Signals, Sep. 2011, Prague, Czech Republic.

Fabian et al., "Comparative Study of Non-Invasive Blood Pressure Measurement Methods in Elderly People", Engineering in Medicine and Biology Society, 2007. EMBS 2007. 29th Annual International Conference of the IEEE , Aug. 22-26, 2007, pp. 612-615.

Smulyan, et al., "Blood Pressure Measurement: Retrospective and Prospective Views", Upstate Med Univ, Div Cardiol, Syracuse, NY, American Journal of Hypertension, 2011, vol. 24, No. 6 (Jun.), pp. 628-634.

Automatic blood pressure monitor Source: http://www.med-help.net/ms-automatic-blood-pressure-monitor.html Date Accessed: Aug. 16, 2012.

International Preliminary Report on Patentability and Written Opinion for PCT Application No. PCT/US2015/015861, issued Aug. 23, 2016, 8 pages.

* cited by examiner

SYSTEMS AND METHODS FOR BLOOD PRESSURE MEASUREMENT

TECHNICAL FIELD

This application is directed to systems and methods for monitoring a patient, and in particular, to systems and methods for determining a hemodynamic parameter associated with the patient.

BACKGROUND

Traditional non-invasive blood pressure monitoring devices operate by inflating a cuff to a pressure well above a patient's systolic blood pressure. Because the systolic pressure is usually not known prior to inflation, the cuff must be inflated to such a high pressure to ensure that the patient's arterial blood flow is completely occluded. Once well above systole, the cuff is deflated and the systolic and diastolic pressures are calculated based on signals provided during cuff deflation.

However, inflating the cuff to such elevated pressures can be uncomfortable for patients. As a result, systems and methods have been developed to determine blood pressures during cuff inflation. These methods, however, are generally inaccurate and/or slow. Consequently, such methods cannot provide a commercially useful determination of systolic pressure that must meet certain regulatory standards.

Other systems and methods have been developed to automatically take a sequence of systolic and diastolic blood pressure measurements, and to estimate blood pressure based on an average of the measured systolic and diastolic blood pressures. For example, U.S. Pat. No. 6,602,199 ("the '199 patent") teaches a system configured to take a predetermined number of consecutive systolic and diastolic blood pressure measurements of a patient. The system of the '199 patent includes a blood pressure cuff, a sensor, and a control module configured to determine an estimated blood pressure of the patient based on the sequence of measurements.

While the system of the '199 patent may provide a rough estimate of patient blood pressure, such systems are typically characterized by several significant drawbacks when used in patient monitoring environments. For example, such systems typically take measurements over a span of several minutes before determining the estimated blood pressure value. In hospitals, physicians' offices, clinics, and other like healthcare facilities, however, such a long lead time prior to determining the blood pressure measurement may result in extended patient wait times and an overall decrease in facility efficiency. Additionally, taking measurements over such a prolonged period can further increase patient discomfort.

The various example embodiments of the present disclosure are directed toward overcoming one or more of the deficiencies of the prior art.

SUMMARY

In an example embodiment of the present disclosure, a method of determining a blood pressure of a patient without completely occluding a blood vessel of the patient includes determining a plurality of pressure pulses, wherein each pressure pulse of the plurality of pressure pulses comprises a profile having a maximum profile height. The method also includes determining a pulse score associated with the plurality of pressure pulses, wherein the pulse score is determined by at least one algorithm based on the profiles of the pressure pulses and the maximum profile heights. The method further includes determining that the pulse score is above a pulse score threshold, and generating, in response to determining that the pulse score is above the pulse score threshold, a pulse curve based on the maximum profile heights. The method also includes determining the blood pressure of the patient, wherein the blood pressure is determined by the at least one algorithm based on a plurality of values corresponding to respective points on the pulse curve.

In another example embodiment of the present disclosure, a blood pressure measurement system includes a sensor configured to determine a plurality of pressure pulses of a patient, wherein each pressure pulse of the plurality of pressure pulses comprises a profile having a maximum profile height. The system also includes a controller operably connected to the sensor. The controller is configured to determine a pulse score associated with the plurality of pressure pulses, wherein the pulse score is determined by at least one algorithm of the controller based on the profiles of the pressure pulses and the maximum profile heights. The controller is also configured to determine that the pulse score is above a pulse score threshold, and to generate, in response to determining that the pulse score is above the pulse score threshold, a pulse curve based on the maximum profile heights. The controller is further configured to determine the blood pressure of the patient without completely occluding a blood vessel of the patient, wherein the blood pressure is determined by the at least one algorithm based on a plurality of values corresponding to respective points on the pulse curve. The system also includes a user interface operably connected to the controller and configured to output the blood pressure.

In a further example embodiment of the present disclosure, a method of manufacturing a blood pressure measurement system includes providing a sensor configured to determine a plurality of pressure pulses of a patient, wherein each pressure pulse of the plurality of pressure pulses comprises a profile having a maximum profile height. The method also includes operably connecting the sensor to a controller. In such an embodiment, the controller is configured to determine a pulse score associated with the plurality of pressure pulses, wherein the pulse score is determined by at least one algorithm of the controller based on the profiles of the pressure pulses and the maximum profile heights. The controller is also configured to determine that the pulse score is above a pulse score threshold, and to generate, in response to determining that the pulse score is above the pulse score threshold, a pulse curve based on the maximum profile heights. The controller is also configured to determine the blood pressure of the patient without completely occluding a blood vessel of the patient, wherein the blood pressure is determined by the at least one algorithm based on a plurality of values corresponding to respective points on the pulse curve. Such a method also includes operably connecting a user interface to the controller, wherein the user interface is configured to output the blood pressure.

Additionally, such an example method includes operably connecting a cuff to the controller, the cuff being selectively inflatable around a limb of the patient. Such a method further includes operably connecting a memory to the controller, the memory including a stored pressure threshold and stored sets of profile heights. In such an embodiment, the controller is configured to compare each maximum profile height to the pressure threshold, identify a subset of the maximum profile heights having a value greater than the pressure threshold, and match the subset of the maximum profile heights with at least one set of the stored sets of profile heights. Moreover, in such an embodiment, the memory further includes a stored set of values corresponding to points on a predetermined pulse curve, and the controller is configured to compare the plurality of values to the stored set of values, and to determine the blood pressure in response to the comparison.

DETAILED DESCRIPTION

Figure 1:
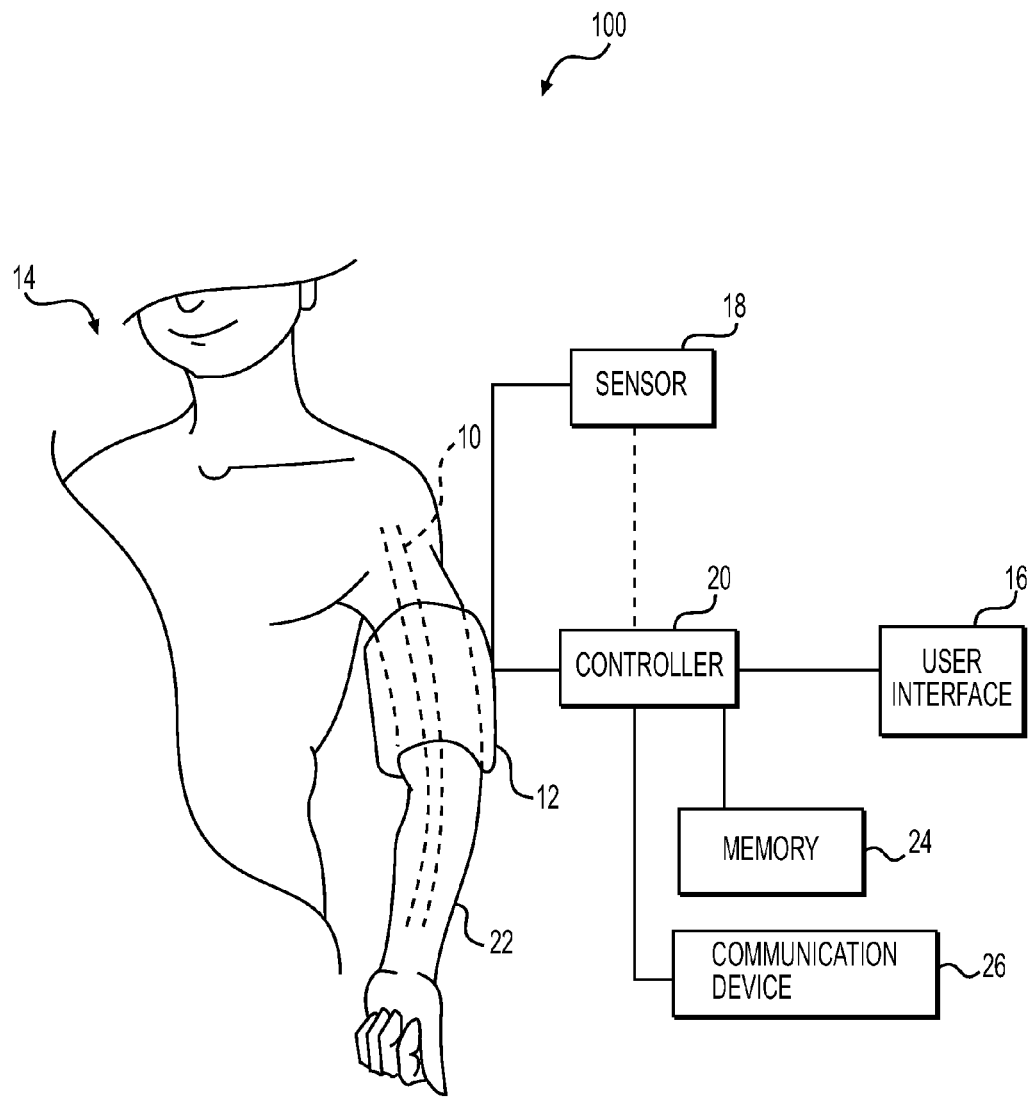
FIG. 1 illustrates a patient monitoring system according to an example embodiment of the present disclosure.

FIG. 1 illustrates a patient monitoring system 100, according to an example embodiment of the present disclosure. The system 100 can be configured to monitor a patient, and in some embodiments, to determine a hemodynamic parameter of the patient. As used herein, the term "hemodynamic parameter" can include an indication of cardiac or vascular health, such as, for example, an indication of cardiac, circulatory, or vascular functionality. Specifically, a hemodynamic parameter can include a heart rate, a blood pressure, a vessel compliance, a saturation of hemoglobin with oxygen in arterial blood (i.e., an $SpO_2$ measurement), an aortic index, an augmentation index, reflected wave ratio, or an indication of treatment. Blood pressure can include systolic, suprasystolic, diastolic, or mean atrial pressure. It is understood that such blood pressures may be represented as a systolic blood pressure over a diastolic blood pressure, and that a mean or average blood pressure may be represented as an average systolic blood pressure over an average diastolic blood pressure. Moreover, an indication of treatment can include a parameter reflecting the affect of a drug treatment, or one or more treatments of a disease state.

The system 100 can include a cuff 12 configured to at least to partially occlude the movement of blood through a blood vessel 10 of a patient 14 such as an artery, vein, or the like. In some embodiments, the cuff 12 can be configured to completely occlude an artery of patient 14. In any of the embodiments described herein, however, the system 100 may be tuned and/or otherwise configured to determine one or more hemodynamic parameters of the patient 14, such as a blood pressure of the patient 14, without completely occluding the blood vessel 10. In such embodiments, the system 100, and/or components thereof, may determine the blood pressure of the patient 14 before the cuff 12 is inflated to a pressure associated with complete occlusion of the blood vessel 10 and/or before a systolic blood pressure of the patient 14 is reached. Although shown in FIG. 1 surrounding an arm 22 of the patient 14, the cuff 12 may be adapted for placement on (i.e., around) any suitable body part of patient 14, including, for example, a wrist, a finger, an upper thigh, an ankle, or any other like limb or body part. In addition, one or more cuffs 12 could be placed at different locations about the patient 14 for use with the system 100.

The cuff 12 can include one or more bladders or other like inflatable devices, and the pressure or volume within the cuff 12 may be controlled by any known inflation device (not shown) operably associated with the cuff 12. Such inflation devices can include a pump or similar device configured to controllably inflate and/or deflate the inflatable device of the cuff 12. For example, such inflation devices could supply the cuff 12 with a fluid to increase the pressure or volume of the cuff 12. In other embodiments, one or more inflation devices could include mechanical, electrical, or chemical devices configured to control vessel occlusion of the patient 14 via the cuff 12. In some embodiments, such inflation devices can inflate the cuff 12 to or towards a target inflation pressure, and may be configured to generally maintain the cuff 12 at any desired inflation pressure for a desired period of time. In some embodiments, the target inflation pressure may be less than or equal to the systolic pressure of the patient 14. Alternatively, in further embodiments the target pressure may be greater than the systolic pressure of the patient 14. In example embodiments, the system 100 may determine the blood pressure of the patient 14 without inflating the cuff to the systolic pressure. Accordingly, even in embodiments in which algorithms, controllers, and/or other components of the system 100 employ a target inflation pressure that is equal to or greater than the systolic pressure, the system 100 may discontinue inflation of the cuff 12 at an inflation pressure less than such a target inflation pressure. Although such embodiments may use a target inflation pressure equal to or greater than the systolic pressure, discontinuing inflation of the cuff 100 at a pressure below such a target inflation pressure may avoid patient discomfort during blood pressure determination.

The system 100 can further include a sensor 18 configured to receive a signal associated with the patient 14. In some embodiments, the sensor 18 can be configured to receive a signal associated with an at least partially occluded vessel 10 of the patient 14. Such an input signal can arise from blood movement through the partially occluded vessel 10 or from a signal associated with an occluded blood vessel 10. The sensor 18 could sample multiple times at various intervals. In yet other embodiments, the sensor 18 could provide an indication of blood vessel movement, such as, for example, oscillations arising from vascular expansion or contraction. For example, the sensor 18 could be configured to detect a pressure or volume of cuff 12 that may vary periodically with the cyclic expansion and contraction of the blood vessel 10 of the patient 14. In particular, the sensor 18 could determine a blood pressure, various pulses of blood through the blood vessel 10, an oxygen saturation of the blood, or any other hemodynamic parameter associated with the patient 14 using an auscultation, oscillometric, or other known measurement method.

In some embodiments, the sensor 18 could detect a volume or a pressure associated with cuff 12. For example, the sensor 18 could include a pressure transducer or other like pressure sensor, and may be located within, on, or about the cuff 12 or other parts of the system 100, such as a controller 20 of the system 100 (described in further detail below). In such embodiments, the sensor 18 may be configured to sense, measure, detect, monitor, calculate, and/or otherwise "determine" one or more blood pressure pulses associated with the patient 14. Each blood pressure "pulse" may be indicative of, for example, the movement of blood through the blood vessel 10 by the heart of the patient 14 during systole, and the number of such pulses per minute may comprise the heart rate of the patient 14.

In example embodiments, the sensor 18 may be configured to determine various aspects, characteristics, and/or configurations of each blood pressure pulse, such as a profile of each pressure pulse and a height of each profile. In example embodiments, the "profile" of a respective pressure pulse may be a two or three-dimensional shape or other like configuration of the pressure pulse, and such a profile may be represented as a distribution of force applied to the cuff 12 (as a result of vascular expansion or contraction of the blood vessel 10) as blood flows through the blood vessel 10. In the context of the present disclosure, the force associated with such pressure pulses may be measured in, for example, mmHg, or any other like metric. Accordingly, the "profile height" of a respective pressure pulse may be a measure of the force applied to the cuff 12 (as a result of vascular expansion or contraction of the blood vessel 10) during the pressure pulse. It is understood that such profiles and/or profile heights may be indicative of a blood pressure of the patient 14. For example, in some embodiments, the blood pressure may be determined by the system 100 based, at least in part, on one or more determined pressure pulses, pulse profiles, and/or profile heights. Moreover, the system 100 could further operate with a plurality of sensors 18, and may include a high-resolution sensor or pneumatic sensor designed to operate in conjunction with cuff 12.

The cuff 12, the cuff inflation devices described above, and/or the sensor 18 may be operably associated with a controller 20. Specifically, the controller 20 may comprise and/or otherwise include one or more processors, microprocessors, programmable logic controllers, and/or other like components configured to control one or more operations of the cuff 12, the cuff inflation devices, and/or the sensor 18. For example, the controller 20 can control inflation and/or deflation of the cuff 12 via control of the inflation devices described above.

In some embodiments, the controller 20 can sense, measure, detect, monitor, calculate, and/or otherwise determine a blood pressure of the patient 14 based on one or more of the hemodynamic parameters determined by the sensor 18. This determination may be based on one or more output signals received from sensor 18, as described above. The controller 20 may also control inflation of cuff 12, inflation of cuff 12 toward a target inflation pressure, or generally maintaining inflation of cuff 12 at about the target pressure. Such a target inflation pressure may be a pressure that is greater than, or equal to, or less than, for example, a systolic pressure of the patient 14 and/or the mean arterial pressure of the patient. For example, as noted above, the system 100 may determine the blood pressure of the patient 14 without inflating the cuff to the systolic pressure. Accordingly, even in embodiments in which the controller 20 employs a target inflation pressure that is equal to or greater than the systolic pressure for purposes of cuff inflation, algorithms of the controller 20 may discontinue inflation of the cuff 12 at an inflation pressure less than such a target inflation pressure. Despite the use of such example target inflation pressures, the controller 20 may determine the blood pressure of the patient 14 without completely occluding the blood vessel 10.

In some embodiments, a hemodynamic parameter such as blood pressure can be determined based on a suprasystolic measurement. In other embodiments, a hemodynamic parameter can be determined based on a first set of data determined during inflation of cuff 12, a second set of data determined during general maintenance of cuff 12 at about the target inflation pressure mentioned above, and/or a third set of data determined during deflation of the cuff 12. These sets of data can include various information included in a signal waveform associated with the patient 14 and/or the cuff 12, and may include amplitude, frequency, morphology, feature, or mathematically derived data. Data can be derived from a derivative, integration, or frequency analysis, such as, for example, a fast-Fourier transform. Data may also be derived from various algorithms, including curve fitting algorithms, neural networks, filtering algorithms, smoothing algorithms, and the like. For example, one or more such algorithms may be utilized by the controller 20 to derive such data.

Although not shown in FIG. 1, in additional example embodiments, the system 100 can optionally include a signal analysis module. For example, the signal analysis module may be configured to analyze one or more signals received from the sensor 18 using one or more processors of the controller 20. For example, the signal analysis module can include one or more filters configured to filter a signal associated with the sensor 18 or the controller 20. Such filters can include band-pass, high-pass, or low-pass filters.

As illustrated in FIG. 1, the system 100 may also include a memory 24 operably connected to the controller 20. The memory 24 may include, for example, a hard drive, a thumb drive, and/or any other like fixed or removable storage device known in the art. Such memory 24 may comprise random access memory, read-only memory, transient memory, non-transient memory, and/or any other like information storage means. In such embodiments, the memory 24 may be configured to store signals, data, values, curves, thresholds, and/or any other like information received from the sensor 18. The memory 24 may also be configured to store signals, data, values, thresholds, curves, and/or any other like information determined by the controller 20 during the various operations described herein. For example, the memory 24 may be configured to store one or more pressure pulses, pulse profiles, pulse heights, pulse curves, target inflation pressures, pressure thresholds, and/or other like information. Additionally, the memory 24 may be configured to store one or more algorithms, protocols and/or other like programs associated with calculating and/or otherwise determining the blood pressure of the patient 14. Additionally, the memory 24 may be configured to store one or more sets of values corresponding to points on one or more pulse curves. Such information may be recalled and/or otherwise utilized by the controller 20 during one or more blood pressure determination methods described herein.

In example embodiments, one or more neural networks may be stored in the memory 24 and operably connected to one or more processors or other components of the controller 20. Alternatively or in addition, one or more neural networks may comprise a component of the controller 20 separate from the memory 24. The neural networks of the present disclosure may comprise interconnected groups of nodes, neurons, or other like processing elements that are operable to perform functions collectively and in parallel. An example neural network of the present disclosure may have three or more layers of neurons. For example, the first layer may include input neurons, which send data via synapses to a second layer of neurons, and then via more synapses to a third layer of output neurons. Additional examples of neural networks may have more layers of neurons with some having increased layers of input neurons and output neurons. Additionally, the neural networks of the present disclosure may include "weights" or other like parameters associated with the various neurons, and such weights may affect the calculations performed by the neural network. The neural networks of the present disclosure may be configured to solve for one or more values, such as the systolic and/or diastolic pressure of the patient 14, using a plurality of different inputs, and such calculations may be non-linear in nature. It is understood that in the example embodiments described herein, the various neural networks of the present disclosure may employ one or more mathematical models, algorithms, or other like protocols to determine, for example, the blood pressure of the patient 14 and/or other like hemodynamic parameters.

The system 100 can further include a user interface 16 configured to provide communication to the patient 14 or one or more operators. For example, the user interface 16 could include a display configured to communicate and/or otherwise output one or more hemodynamic parameters. The user interface 16 may further include one or more speakers or other like audio devices configured to communicate and/or otherwise output information to the patient 14 and/or a user operator of the system 100. In further embodiments, the system 100 may include one or more transmitters, network devices, routers, Bluetooth® devices, WiFi® devices, radio devices, and/or other like communication device 26 configured to transmit data to a remote location and/or to a remote device. In such embodiments, the communication device 26 may enable the transmission of information to or from the controller 20. It is understood, that such communication devices 26 may facilitate the transmission of such information via wired or wireless means. For example, in any of the embodiments described herein, one or more components of the system 100, such as the controller 10, may be disposed remote from a remainder of the components of the system 100. In such embodiments, for example, the controller 20 may be disposed in a different location of a healthcare facility than the cuff 12, user interface 16, or other components of the system 100. Alternatively, in further embodiments, the controller 20 may be in a first healthcare facility and a remainder of the components of the system 100 may be located in a second healthcare facility different from the first facility. In such embodiments, the various components of the system 100 may be in communication and/or otherwise operably connected via the communication devices 26 described herein.

In addition to the components outlined above, the system 100 may include various other components as required, such as, for example, a power source and/or a user input device. One or more components described herein may be combined or may be separate independent components of the system. Moreover, the various components of the system 100 could be integrated into a single processing unit or may operate as separate processors. In operation, one or more processors can be configured to operate in conjunction with one or more software programs to provide the functionality of the system 100. For example, one or more of the components described above with respect to the system 100 may include one or more hardware components and/or one or more software components configured to control operation of such components and/or of the system 100.

Figure 2:
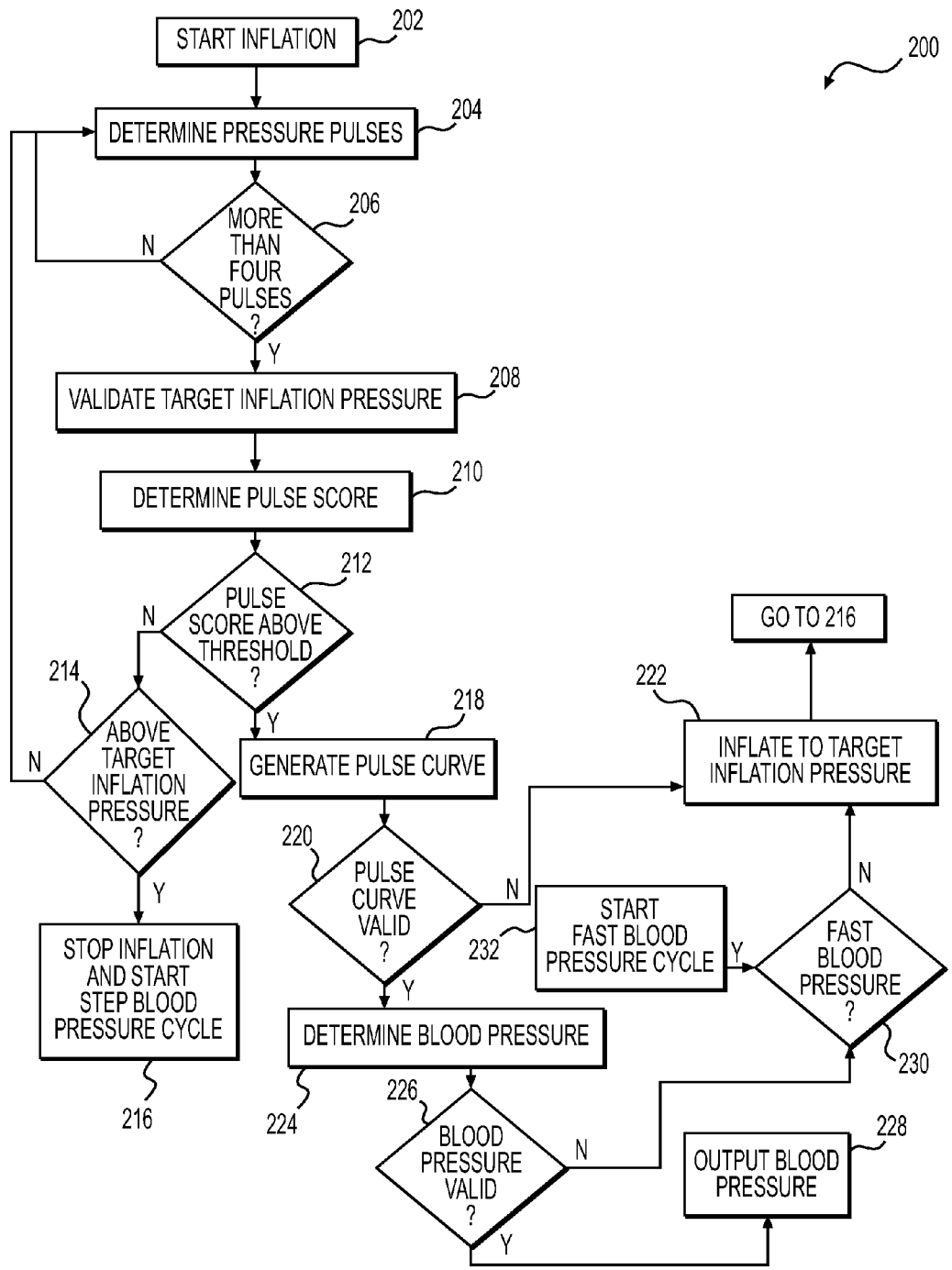
FIG. 2 illustrates a flow chart corresponding to an example method of the present disclosure.

FIG. 2 illustrates a flow chart 200 according to an example embodiment of the present disclosure. Each operation described below with respect to FIG. 2 can be understood as corresponding to one or more computational instructions. These computational instructions can operate based on hardware and/or software components of the system 100, and may operate on one or more processors of the controller 20, and/or on or via the neural network.

In an example embodiment, a method illustrated by the flow chart 200 may include one or more steps required to position, activate and/or calibrate the various components of system 100. For example, the system 100 may be turned on, a calibration protocol may be started, the cuff 12 may be placed around a limb of the patient 14, such as the arm 22, an operator may enter information to identify a particular patient 14, or information could be extracted from a database. Further, various components of the system 100 may be calibrated or tested to ensure proper functioning. These operations could include a check of cuff integrity, a determination as to whether sufficient power is available, a calibration of one or more sensors 18, or a confirmation of proper processor functioning. Also, other information may be entered into the system 100, such as a patient identification, weight, gender, height, prior pulse profiles, prior blood pressure determinations, prior pulse curves, predetermined thresholds, or other suitable data.

At Step: 202, the controller 22 may operate one or more of the inflation devices described above to start inflation of the cuff 12. Once inflation begins at step: 202, such inflation devices may direct pressurized air and/or other like fluid to the cuff 12, thereby increasing an internal pressure of the cuff 12. Such an increase in pressure may result in an increasing level of pressure being applied by the cuff 12 to the limb and/or to the blood vessel 10. It is understood that the cuff 12 may be inflated toward a predetermined target inflation pressure, and such a predetermined target inflation pressure may be greater than, less than, or equal to a known or predicted systolic blood pressure of the patient 14, and inflation of the cuff 12 at step: 202 may result in at least partial occlusion of the blood vessel 10. For example, as illustrated by the example curve 28 of FIG. 3, the pressure applied to the limb by the cuff 12 (i.e., the cuff pressure) may be increased, over time. In some embodiments, the cuff pressure may be increased from below a diastolic pressure of the patient 14 to a pressure less than the target inflation pressure. As noted above, the controller 20 may control inflation of the cuff 12 toward a target inflation pressure that is equal to or greater than the systolic pressure for purposes of cuff inflation. Nevertheless, algorithms employed by the controller 20 may discontinue inflation of the cuff 12 at an inflation pressure less than such a target inflation pressure. As a result, the controller 20 may determine the blood pressure of the patient 14 without completely occluding the blood vessel 10, and without inflating the cuff 12 to the target inflation pressure. In example embodiments, the target inflation pressure may be located at any desirable location along the curve 28.

Figure 4:
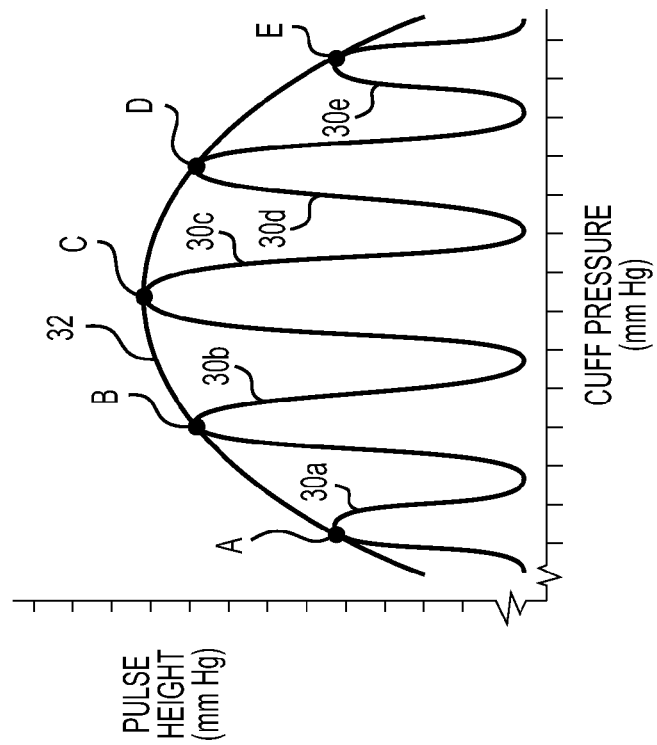
FIG. 4 illustrates a plurality of blood pressure pulse profiles according to an example embodiment of the present disclosure.
Figure 3:
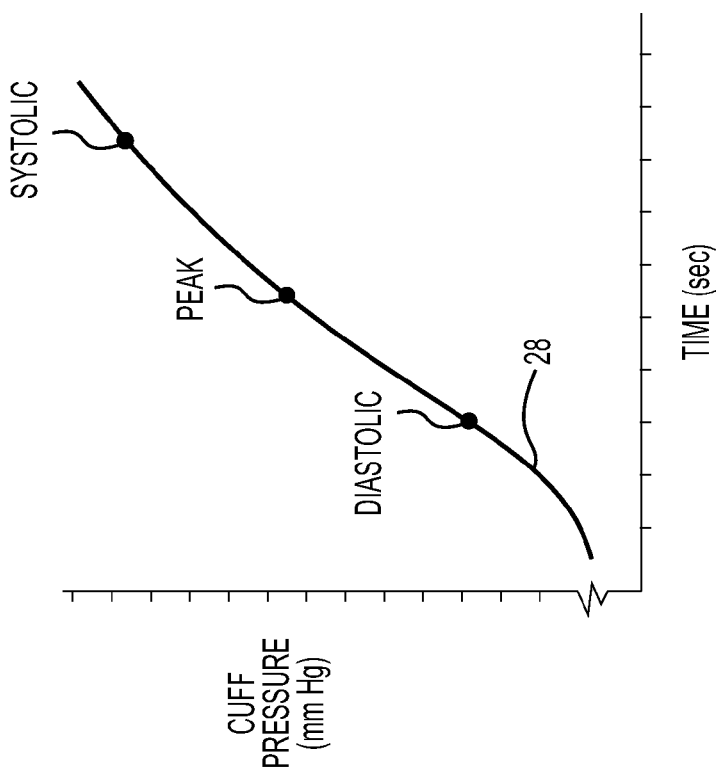
FIG. 3 illustrates an example cuff pressure curve of the present disclosure.

As the cuff 12 is inflated, the sensor 18 may begin to determine one or more blood pressure pulses at step: 204. For example, the sensor 18 may continuously sense the flow of blood passing through the blood vessel 10 as a pressure applied by the cuff 12 to the limb of the patient 14 increases. In particular, the sensor 18 may determine the pressure applied to the cuff 12 by the blood vessel 10 as the blood vessel 10 increases and/or decreases in diameter due to the flow of blood therethrough. As described above, each pressure pulse determined by the sensor 18 may be characterized by a respective pulse profile, and each pulse profile may have a maximum profile height. Example pulse profiles 30a-30e (collectively, "pulse profiles 30") are illustrated in FIG. 4. For example, each of the pulse profiles 30 shown in FIG. 4 includes a respective maximum profile height illustrated by the points A-E shown thereon. It is understood that, as shown in FIG. 4, the maximum profile heights A-E may be referred to herein as "pulse heights" of the respective pressure pulses illustrated by the pulse profiles 30. As noted above, such pulse heights (i.e., the maximum profile height of each pulse profile 30a-30e) may be indicative of the force exerted on the cuff 12 during a corresponding pressure pulse of the plurality of pressure pulses determined by the sensor 18. Additionally, in example embodiments, successive profile heights A-C may increase up to a peak profile height illustrated at point C. For example, the pulse height at point C may be indicative of the maximum force exerted on the cuff 12 during inflation of the cuff 12 from below a diastolic pressure to a pressure less than the target inflation pressure described above. The peak profile height at point C is also shown in FIG. 3, and is located between the systolic and diastolic pressure of the patient on the curve 28. As the cuff pressure increases beyond a pressure corresponding to the peak profile height illustrated at point C, the profile heights of the successive pulse profiles 30 may decrease, as shown by points D and E.

Figure 5:
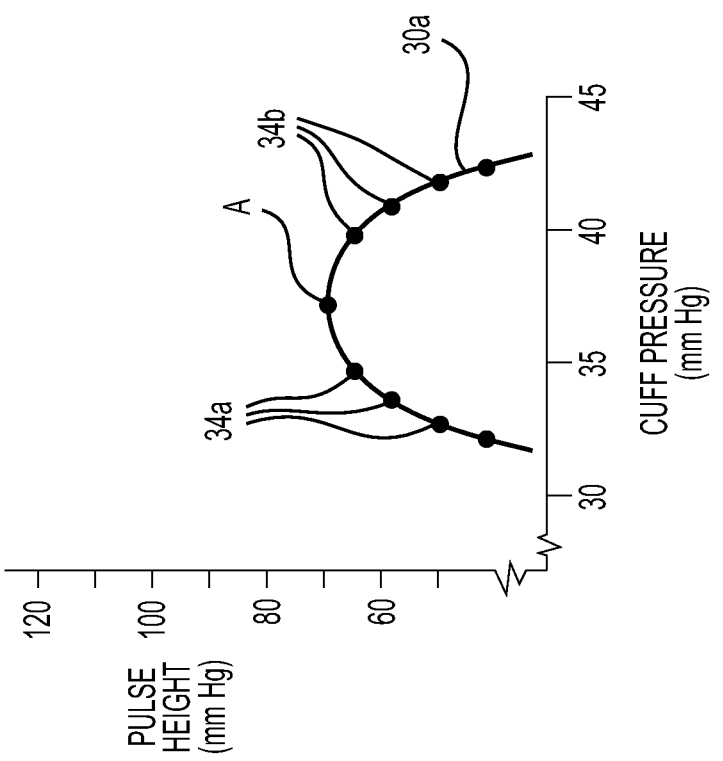
FIG. 5 further illustrates an example blood pressure pulse profile of FIG. 4.
Figure 6:
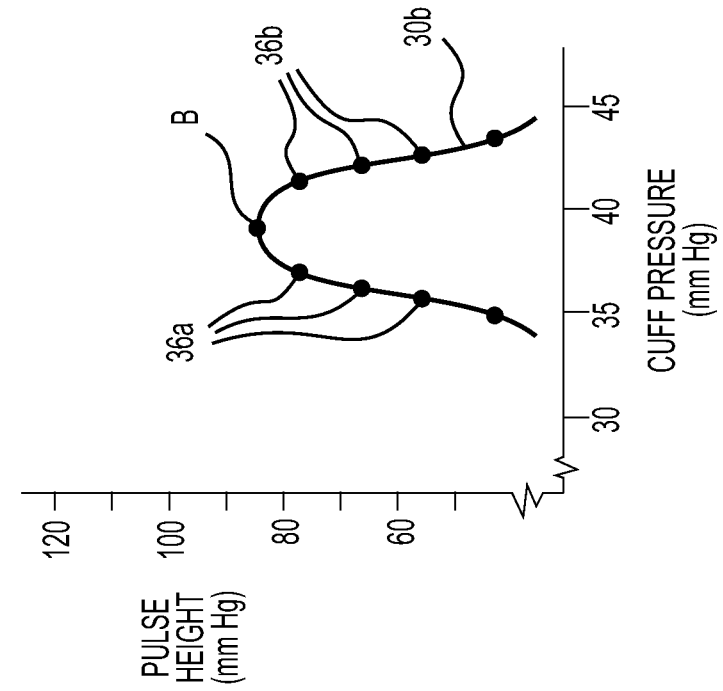
FIG. 6 further illustrates another example blood pressure pulse profile of FIG. 4.
Figure 7:
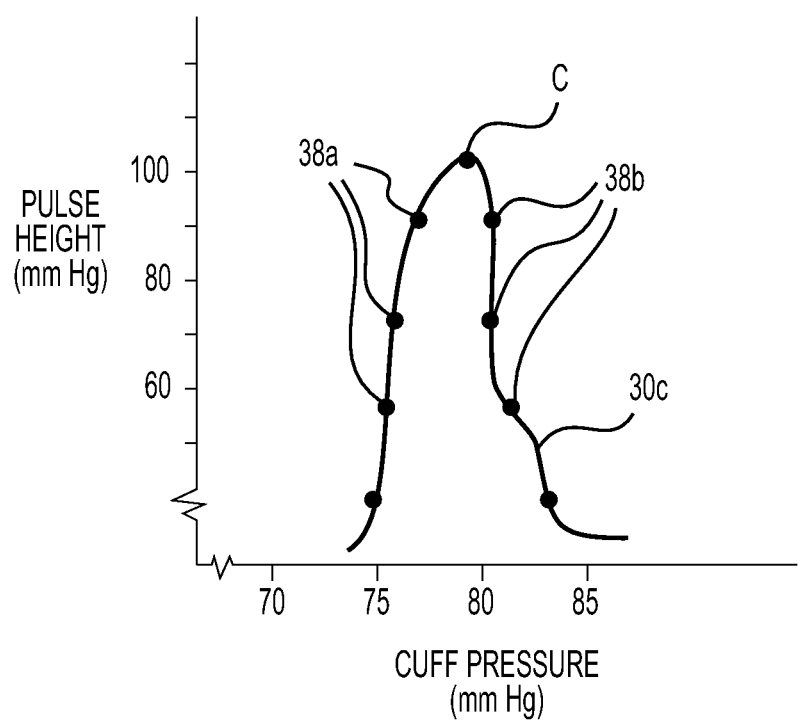
FIG. 7 further illustrates yet another example blood pressure pulse profile of FIG. 4.

Each of the pulse profiles 30 described herein may be defined by a plurality of values indicative of the force exerted on the cuff 12 during a corresponding pressure pulse of the plurality of pressure pulses, and such force may be the result of blood flow through the limb of the patient 14. FIGS. 5-7 illustrate the example pulse profiles 30a-30c in greater detail. As shown by the example pulse profile 30a of FIG. 5, each value of the plurality of values may comprise a pulse height that is determined at a respective cuff pressure, and such values may be represented by respective points 34a, 34b on the pulse profile 30a. In such an embodiment, each value corresponding to the points 34a, 34b may be less than the pulse height value corresponding to the maximum profile height A. Similarly, as shown by FIG. 6 and FIG. 7, respectively, values corresponding to the points 36a, 36b of the pulse profile 30b may be less than the pulse height value corresponding to the maximum profile height B, and values corresponding to the points 38a, 38b of the pulse profile 30c may be less than the pulse height value corresponding to the maximum profile height C. Accordingly, in example embodiments, each of the pulse profiles 30 may comprise best-fit curves formed based on the corresponding pulse height values associated therewith. Additionally, it is understood that at relatively low cuff pressures, such as those associated with FIG. 5, an example pulse profile 30a may be relatively rounded. As such cuff pressures increase, such as during inflation of the cuff 12, example pulse profiles 30 may become taller, narrower, and more spike-like. Such example relatively tall, relatively narrow, and/or relatively spike-like configurations are illustrated by the pulse profiles 30b, 30c shown in FIGS. 6 and 7. In such embodiments, the shape of the pulse profile 30 may be indicative of, for example, the commencement and degree of intra-heart cycle occlusion of the blood vessel 10. As used herein, the term "intra-heart cycle" may refer to, for example, an intra-cardiac cycle, a cardiac-output cycle, or any other like cycle or period of time indicative of a full pulse or heartbeat. For example, the shape of the pulse profile 30 may transition from the relatively rounded shape shown in FIG. 5 to the relatively tall, narrow, spike-like shape shown in FIG. 7. As the blood vessel 10 transitions from fully unoccluded to at least partially occluded. Moreover, the development of a step, flat portion, notch, or other like feature or irregularity in the shape of the pulse profile, such as the step shown in the pulse profile 30c of FIG. 7 (proximate the "30c" identifier), may indicate that the maximum profile height C of the respective pulse profile 30c is greater than or approximately equal to the mean arterial pressure of the patient 14 and/or the peak pressure described above with respect to FIG. 3. In such embodiments, the system 100 may be tuned to recognize such a change in profile shape, and may discontinue cuff inflation in response to such a change in shape in order to minimize patient discomfort.

In example embodiments, the pressure pulses described herein may be determined at step: 204 during inflation of the cuff 12 and/or prior to the cuff 12 being substantially completely inflated. Likewise, as noted above, the pressure pulses, pulse profiles 30, maximum profile heights A-E, and/or other parameters described herein may be determined while the blood vessel 10 is only partially occluded, and in such example embodiments, one or more such determinations may be made during transition of the blood vessel 10 of the patient 14 from unoccluded to at least partially occluded. Accordingly, the pressure pulses, pulse profiles 30, maximum profile heights A-E, and/or other parameters described herein may be determined prior to occluding the blood vessel 10.

In example embodiments, the system 100 may minimize the number of pressure pulses needed to determine the blood pressure of the patient 14. Such a minimum number (i.e., a "target number") of pressure pulses may be selected in order to ensure the accuracy and reliability of the resulting blood pressure. Ideally, the target number of pressure pulses may be minimized in order to reduce the amount of time required for such a blood pressure determination and also to minimize the level of patient discomfort associated with the determination. It is understood that patient conditions such as an abnormally low blood pressure (for example, a systolic blood pressure of 60 mmHg or less, and/or a diastolic blood pressure of 40 mmHg or less), an abnormally low heart rate, or other like conditions may make it more difficult for the sensor 18 to determine pressure pulses at step: 204. Such conditions may, thus, reduce the reliability of some blood pressure determinations.

Accordingly, at step: 206, the controller 20 may determine whether a target number of pressure pulses have been determined by the sensor 18. In such an embodiment, the target number of pressure pulses may be four, however, in further example embodiments, such a minimum number of pressure pulses may be greater than or less than four. If, at step: 206 the controller 20 determines that the target number of pressure pulses have not been determined (step: 206—no), control may proceed to step: 204. If, on the other hand, at step: 206 the controller 20 determines that the target number of pressure pulses have been determined, (step: 206—yes), control may proceed to step: 208 where the controller 20 may validate a predetermined target inflation pressure. For example, the controller 20 may be operable to inflate the cuff 12 toward a predetermined target inflation pressure of approximately 160 mmHg, and such a target inflation pressure may be appropriate for most patients 14. In some situations, however, such a target inflation pressure may need to be increased or decreased depending on the profile heights and/or other characteristics of the pressure pulses determined at step: 204. As noted above, in example embodiments, the controller 20 may not fully inflate the cuff 12 to such a target inflation pressure due to patient discomfort.

In example embodiments, the validation procedure occurring at step: 208 may include comparing each maximum profile height A-E of the successive pulse profiles 30 with one or more pressure thresholds. In such embodiments, the target inflation pressure may remain unchanged as long as the maximum profile heights A-E under evaluation are below a first pressure threshold. If one or more maximum profile heights A-E of the pulse profiles 30 have a pulse height value greater than the first pressure threshold, the controller 20 may, at step: 208, identify a subset of the maximum profile heights A-E having such a value, and may match the identified subset of maximum profile heights with a stored set of profile heights. By doing so, the controller 20 may correlate the pressure pulses determined at step: 204 to a plurality of previously determined pressure pulses stored in the memory 204. In such embodiments, the stored set of profile heights may include a corresponding stored target inflation pressure. As a result, at step: 208, the controller 20 may continue inflation of the cuff 12 toward the stored target inflation pressure corresponding to the stored set of profile heights. In such an example, the original predetermined target inflation pressure may be replaced with the stored target inflation pressure.

In example embodiments, the pressure thresholds utilized at step 208 may comprise a minimum pressure threshold that is predetermined and/or otherwise selected in order to ensure that the target inflation pressure utilized by the controller 20 for inflation of the cuff 12 is always maintained above the cuff pressure corresponding to the maximum profile height of the previous (i.e., the most recent) pressure pulse determined at step: 204. In example embodiments, such a pressure threshold may be equal to approximately 100 mmHg. In further example embodiments, however, such a pressure threshold may be greater than or less than approximately 100 mmHg. Additionally, the matching procedure utilized by the controller 20 at step 208 may include comparing the maximum profile height A-E of each of the pulse profiles 30 to a plurality of stored sets of profile heights, and selecting a stored set from the plurality of stored sets of profile heights. The controller 20 may make such a selection based on the maximum profile height A-E of each of the pulse profiles 30 being within a predetermined range of the selected stored set of profile heights.

At step: 210, the controller 20 may determine one or more pulse scores associated with the plurality of pressure pulses determined at step: 204. Such pulse scores may be determined by the one or more algorithms stored in memory 24 and/or otherwise associated with the controller 20. In some embodiments, one or more neural networks may be used at step: 201 to determine such pulse scores. Regardless of the protocol utilized, the controller 20 may determine the one or more pulse scores based on, for example, the various pulse profiles 30 and/or the maximum profile heights A-E corresponding thereto. For example, at step: 210, the controller 20 may select a predetermined number of pressure pulses for analysis and/or for determining the pulse score. In such an analysis, the controller 20 may identify and/or otherwise select three or more of the most recently determined pressure pulses 30 for analysis at step: 210. For example, with reference to the pulse profiles 30a-30c shown in FIG. 5, the controller 20 may generate a first set of reference values by averaging the pulse height values corresponding to points 34a, 34b of the pulse profile 30a with the corresponding values corresponding to points 36a, 36b of the pulse profile 30b. In some embodiments, the controller 20 may generate a first reference curve (not shown) by averaging such values to generate the first set of reference values, and by plotting the first set of reference values in a way similar to that shown in FIGS. 5-7. In such an embodiment, the first reference curve may be defined by the first set of reference values.

Additionally, at step: 210, the controller 20 may generate a second set of reference values by subtracting the values corresponding to points 38a, 38b of the pulse profile 30c from the corresponding values of the first set of reference values. In some embodiments, the controller 20 may generate a second reference curve (not shown) by, for example, subtracting the values corresponding to points 38a, 38b of the pulse profile 30c from the corresponding values of the first set of reference values, and by plotting the second set of reference values in a way similar to that shown in FIGS. 5-7. In such an embodiment, the second reference curve may be defined by the second set of reference values. Additionally, in such an embodiment, the controller 20 may determine the pulse score at step: 210 by using the second set of reference values and the maximum profile heights A-C of the pulse profiles 30a-30c as inputs to the one or more algorithms noted above. In such embodiments, the pulse score may comprise an output of such algorithms.

Additionally, in such embodiments, the pulse score may comprise an indication of the likelihood that the most recent maximum profile height C comprises the peak pressure described above with respect to FIG. 3. For example, the plurality of pulses determined at step: 204 may collectively be referred to by healthcare professionals as defining a "blood pressure envelope" of the patient 14. Additionally, the maximum profile height C (i.e., the peak pressure of the blood pressure envelope) may correlate strongly to the mean arterial pressure of the patient 14 in most embodiments. In order to optimize the accuracy of the blood pressure determinations performed by the system 100, it may be desirable to confirm that this peak pressure (the maximum profile height C) has been reached. Accordingly, the pulse score determined at step: 210 may be an indication of the likelihood that the cuff pressure has been increased to a level at which the peak pressure of the blood pressure envelope has been reached.

It is understood that the pulse score determined at step: 210 may be any numeric and/or alphanumeric score, and such a pulse score may be associated with any known scale. For example, the pulse score determined at step: 210 may be on a scale of 0-3, where a pulse score equal to 3 may be indicative of an approximately 100% likelihood that the current cuff pressure is above a cuff pressure corresponding to the peak pressure of the present blood pressure envelope. In such an example scale, a pulse score equal to 2 may be indicative of an approximately 90% likelihood that the current cuff pressure is above a cuff pressure corresponding to the peak pressure of the present blood pressure envelope, and so on. It is understood that in further example embodiments, any alternative scale may be utilized by the controller 20 at step: 210.

At step: 212, the pulse score may be compared to one or more pulse score thresholds to determine whether the present blood pressure envelope is mature enough for accurately determining the blood pressure of the patient 14. For example, at step: 212 the controller 20 may determine whether the pulse score determined at step: 210 is above a predetermined minimum pulse score threshold. Such a predetermined pulse score threshold may be, for example, a relatively high minimum threshold in order to ensure sufficient maturity of the blood pressure envelope. For example, in embodiments in which the scale of 0-3 described above is utilized for such determinations at step: 212, the pulse score threshold may be greater than or equal to 2.5. Such a relatively high pulse score threshold may permit determination of patient blood pressure only if the determined pulse score is indicative of a 95% likelihood that the current cuff pressure is above a cuff pressure corresponding to the peak pressure of the present blood pressure envelope.

If the pulse score is not above the pulse score threshold (step: 212—no), control may proceed to step: 214 where the controller 20 may determine whether the present cuff pressure is above the target inflation pressure described above. If the present cuff pressure is not above the target inflation pressure (step: 214—no), control may proceed to step: 204. If, on the other hand, the present blood pressure envelope has matured such that the present cuff pressure is above the target inflation pressure (step: 214—yes), control may proceed to step: 216 where the controller 20 may control the inflation devices to stop inflation of the cuff 12. Since, in some embodiments, it may be desirable to determine the blood pressure of the patient 14 without inflating the cuff 12 to the target inflation pressure, stopping inflation at step: 216 may assist in minimizing patient discomfort. Additionally, at step: 216 the controller 20 may begin an alternate blood pressure determination process or protocol. Such an alternative blood pressure determination process may include, for example, a process in which the systolic and/or diastolic blood pressure of the patient 14 may be determined as the cuff 12 is deflated.

Figure 8:
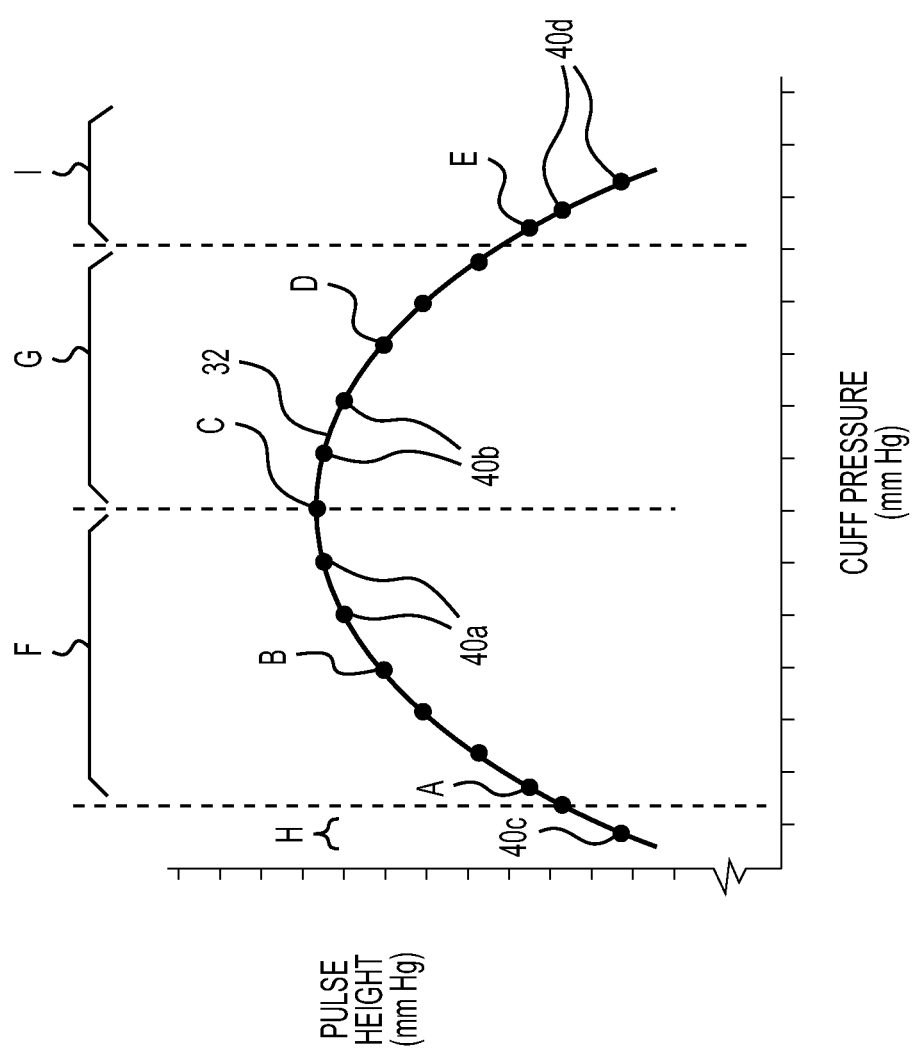
FIG. 8 illustrates an example pulse curve of the present disclosure.

If the controller 20 determines, at step: 212, that the pulse score determined at step: 210 is above the pulse score threshold (step: 212—yes), the controller 20 may generate, in response to such a determination, one or more pulse curves based on, for example, one or more of the maximum profile heights A-E illustrated in FIG. 4. For example, at step: 218, the controller 20 may form a best-fit curve using the pulse height values corresponding to the maximum profile heights A-D, and such an example pulse curve 32 is illustrated in FIG. 8. While in the example embodiment illustrated in FIG. 8, each of the maximum profile heights A-D comprise respective points on the pulse curve 32, in additional example embodiments, one or more of the maximum profile heights A-D may comprise points that are not disposed on the pulse curve 32. It is understood that such a best-fit curve may be generated at step: 218 using a polynomial fit, a least-squares fit, and/or any other known statistical algorithm or process of forming a curve based on a plurality of values. It is also understood that, in some embodiments, portions of the pulse curve 32 may be formed by extrapolation and/or other known techniques. For instance, portions of the pulse curve 32 before the maximum profile height A and after the maximum profile height D may, in some embodiments, be formed based on the shape and/or other characteristics of the corresponding pulse profiles 30 described above. Such extrapolated portions of the pulse curve 32 are illustrated with a dashed line in FIG. 8.

At step: 220, the controller 20 may determine whether the pulse curve 32 generated at step: 218 has a "valid" profile. For example, step 220 may comprise a quality check utilized to determine whether the pulse curve 32 is representative of a realistic blood pressure envelope of the patient 14. Such a quality check may be based on, for example, experience, information, and/or knowledge gained over time and associated with pulse curves 32 previously determined by the system 100. Based on such a validity determination, the controller 20 may be configured to determine whether the current blood pressure determination method should be continued or, instead, whether an alternative blood pressure determination process or protocol should be employed.

For example, at step: 220, the controller 20 may compare a plurality of values corresponding to points on the pulse curve 32 to a stored set of values corresponding to respective points on a predetermined pulse curve (not shown). In such an example embodiment, the points on the pulse curve 32 may comprise one or more of the maximum profile heights A-D, and the values corresponding to the points A-D may be pulse height values corresponding to the points A-D. Additionally, the predetermined pulse curve described above may comprise a known pulse curve having an acceptable profile. Such an acceptable profile may, for example, be characterized by a relatively smooth and/or relatively rounded shape, similar to the shape of the pulse curve 32 illustrated in FIG. 8. The comparison and validation process at step: 220 may be substantially similar to the process described above with respect to step: 208. For example, at step: 220 the controller 20 may determine whether the plurality of values associated with points on the pulse curve 32 are within a predetermined acceptable range of the corresponding values associated with points on the predetermined pulse curve. Such an acceptable range may be relatively narrow to ensure a relatively high degree of accuracy in such a validity determination. For example, such an acceptable range may be equal to approximately 3 percent or less. Further, such a determination may be made on a point-by-point basis. Alternatively, such a validity determination may be made based on whether a majority of the values associated with the pulse curve 32 are within the predetermined acceptable range. In still further embodiments, any other known additional metric may be utilized for such a determination. If the controller 20 determines, at step: 220, that the determined pulse curve 32 is not valid (step: 220—no), control may proceed to step: 216.

If, on the other hand, the controller 20 determines, at step: 220, that the determined pulse curve 32 is valid (step: 220—yes), control may proceed to step: 224, where the controller 20 may determine the blood pressure of the patient 14 in response to the comparison and/or the validity determination made at step: 220. In example embodiments, the controller 20 may utilize the one or more algorithms noted above to determine the blood pressure at step: 224 based at least in part on a plurality of values corresponding to respective points on the pulse curve 32 generated at step: 218. As noted above, such respective points on the pulse curve 32 may comprise one or more of the maximum profile heights A-D. In example embodiments, the plurality of values utilized to determine the blood pressure at step: 224 may also include pulse height values corresponding to additional points 40*a*-40*b* on the pulse curve 32. It is understood that such values may comprise inputs to the one or more algorithms at step: 224, and the determined blood pressure may comprise an output of such algorithms. As noted above, such a determined blood pressure may comprise a systolic pressure over a diastolic pressure.

In some embodiments, the controller 20 may determine such a blood pressure utilizing only a subset of the values corresponding to points on the pulse curve 32. In such embodiments, the controller 20 may omit values corresponding to a remainder of the points on the pulse curve 32 from such a blood pressure determination. For example, providing the one or more algorithms with inputs that are consistent relative to, for example, the peak pressure corresponding to the maximum profile height C may increase the accuracy of the blood pressure determination. As a result, in some embodiments the controller 20 may utilize the peak pressure value corresponding to the maximum profile height C as an input to the one or more algorithms at step: 224. The controller 20 may also identify one or more subsets of values corresponding to points on the pulse curve 32 for use as inputs to the neural network at step: 224, and the subsets of values may be identified relative to, for example, the peak pressure value corresponding to the maximum profile height C.

For example, as illustrated in FIG. 8, a first subset of values may include pulse height values corresponding to points on a first section F of the pulse curve 32 before the point C. Such an example first subset of values may include pulse height values corresponding to maximum profile heights A and B, as well as one or more points 40a. Additionally, a second subset of values may include pulse height values corresponding to points on a second section G of the pulse curve 32 after the point C. Such an example second subset of values may include pulse height values corresponding to maximum profile height D, as well as one or more points 40b. As shown in FIG. 8, the second subset of values may be exclusive of the first subset of values, and in such embodiments, the controller 20 may determine the blood pressure of the patient at step: 224 by using the first and second subsets of values, as well as the peak pressure value corresponding to the maximum profile height C, as inputs to the one or more algorithms, neural networks, or other protocols described above.

In example embodiments, values corresponding to points on the pulse curve 32 that are outside of sections F and G may be omitted from the blood pressure determination at step: 224. For example, a third subset of values may include pulse height values corresponding to points on a third section H of the pulse curve 32. Such an example third subset of values may include pulse height values corresponding to one or more points 40c. Additionally, a fourth subset of values may include pulse height values corresponding to points on a fourth section I of the pulse curve 32, and such an example fourth subset of values may include pulse height values corresponding to maximum profile height E, as well as one or more points 40d. In such embodiments, the pulse height values corresponding to points on the third and fourth sections H, I of the pulse curve 32 may comprise a remainder of values, and such values may be exclusive of values corresponding to points on the first and second sections F, G of the pulse curve 32. As noted above, the controller 20 may determine the blood pressure at step: 224 without this remainder of values.

At step: 224 the controller 20 may truncate, partition, and/or otherwise divide the pulse curve 32 in any number of ways in order to facilitate providing consistent information as inputs to, for example, the one or more algorithms. For example, the controller 20 may identify the first and second sections F, G of the pulse curve 32 by selecting a first percentage of points on the pulse curve 32 before the maximum profile height C, and a second percentage of points on the pulse curve 32 after the maximum profile height C. For example, the controller 20 may select between approximately 50% and approximately 80% of the points on the pulse curve 32 before the point C, and may utilize the pulse heights corresponding to such points as inputs to the one or more algorithms. In such an embodiment, section F of the pulse curve 32 may comprise the section of the pulse curve 32 that includes approximately 60% of the points (such as, points 40a, and maximum profile heights A and B) on the pulse curve 32 before the point C. Likewise, the controller 20 may select between approximately 10% and approximately 30% of the points on the pulse curve 32 after the point C, and may utilize the pulse heights corresponding to such points as inputs to the one or more algorithms. In such an embodiment, section G of the pulse curve 32 may comprise the section of the pulse curve 32 that includes approximately 20% of the points (such as, points 40b and the maximum profile height D) on the pulse curve 32 after the point C. It is understood that the percentages described above with regard to sections F and G are merely example, and that in further embodiments, different percentages may be utilized by the controller 20 to truncate, partition, and/or otherwise divide the pulse curve 32.

At step: 226, the controller 20 may confirm the "validity" of the blood pressure determined at step: 224. As noted above with respect to step: 220, the controller 20 may determine validity in any number of ways. For example, at step: 226 the controller 20 may compare the blood pressure determined at step: 224 to one or more blood pressure thresholds associated with valid and/or invalid pressures. In such an embodiment, the controller 20 may determine that the blood pressure output by the one or more algorithms is valid if the blood pressure is less than a maximum blood pressure threshold and is greater than a minimum blood pressure threshold. In embodiments in which the blood pressure determined by the one or more algorithms comprises a systolic pressure and a diastolic pressure, the controller 20 may compare the systolic pressure output by the one or more algorithms to a maximum systolic pressure threshold and to a minimum systolic pressure threshold. The controller 20 may also compare the diastolic pressure output by the one or more algorithms to a maximum diastolic pressure threshold and to a minimum diastolic pressure threshold. In such embodiments, the controller 20 may determine that the systolic and diastolic pressures are valid at step: 226 (step: 226—yes) only if the systolic pressure is between the maximum and minimum systolic pressure thresholds, and the diastolic pressure is between the maximum and minimum diastolic pressure thresholds. In response to making such a determination, control may continue to step: 228 where the controller 20 may output the blood pressure determined at step: 224 via, for example, the user interface 16. It is understood that such an output may comprise a visual indication of the blood pressure and/or an audible indication of the blood pressure.

If, on the other hand, the controller 20 determines that the systolic pressure is outside of the maximum or minimum systolic pressure thresholds, or that the diastolic pressure is outside of the maximum or minimum diastolic pressure thresholds (step: 226—no), the controller 20 may operate one or more of the inflation devices to discontinue inflation of the cuff 12 without outputting the blood pressure determined at step: 224. For example, in response to such a determination, control may proceed to step: 216 where the controller 20 may determine the blood pressure using an alternate blood pressure determination method. Various example aspects of such alternate blood pressure determination methods are disclosed in co-owned U.S. patent application Ser. No. 12/650,984, and co-owned U.S. Pat. Nos. 7,429,245 and 8,197,414, the entire disclosures of which are expressly incorporated herein by reference.

In some embodiments, the controller 20 may also be configured to streamline the blood pressure determination process in situations where a patient 14 is being monitored over an extended period of time. For example, in situations where the condition of the patient 14 is being monitored prior to and/or after surgery, during an extended hospital stay, and/or in other like circumstances, the controller 20 may be configured to substantially continuously monitor the blood pressure of the patient 14 over a span of hours or days. In such situations, it may be desirable to minimize the discomfort associated with repeated blood pressure determination cycles. Accordingly, upon determining the pulse curve 32 at step: 220 and determining the blood pressure of the patient 14 at step: 224, the controller 20 may be configured to determine the blood pressure of the patient 14 in future blood pressure determination cycles based on a comparison between the initial pulse curve 32 determined at step: 220 and later-determined pulse curves.

For example, in a situation in which an initial blood pressure and an initial pulse curve 32 has been determined, in future blood pressure determination cycles, the controller 20 may generate an additional pulse curve in accordance with steps: 202-220. Such an additional pulse curve may be based on, for example, an additional plurality of pressure pulses, each having a unique pulse profile and a corresponding maximum profile height. The controller 20 may then compare the pulse height values corresponding to the points 40a, 40b on the initial pulse curve 32 with the pulse height values corresponding to points on the additional pulse curve.

Figure 9:
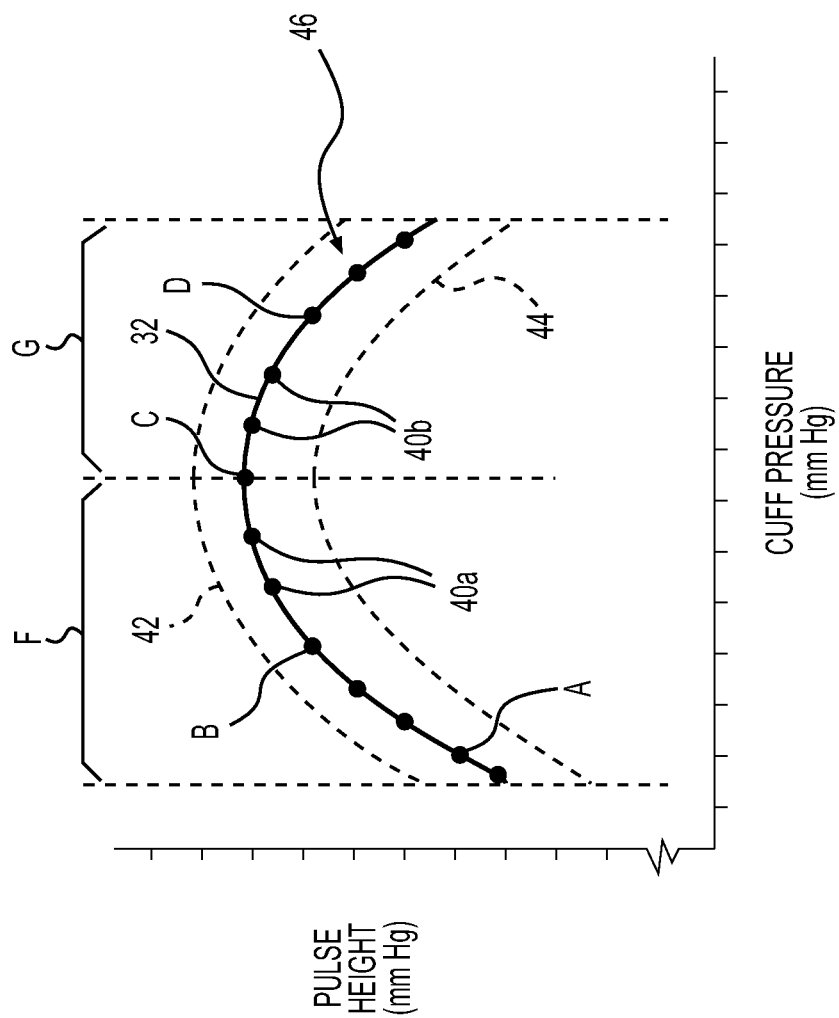
FIG. 9 further illustrates the example pulse curve of FIG. 8.

For example, FIG. 9 illustrates the initial pulse curve 32 described above. FIG. 9 also illustrates example upper and lower pulse curve thresholds 42, 44. The upper and lower pulse curve thresholds 42, 44 may define, for example, upper and lower bounds of an acceptable pulse height range 46. In such an embodiment, the controller 20 may compare, for example, the maximum profile heights of the additional plurality of pressure pulses with the maximum profile heights A-D of the initial pulse curve 32 shown in FIG. 9. If all and/or a majority of the maximum profile heights of the additional plurality of pressure pulses are within the acceptable pulse height range 46, the controller 20 may output the blood pressure determined at step: 224 in the blood pressure determination cycle during which the additional plurality of pressure pulses were determined. In such an embodiment, the controller 20 need only control inflation of the cuff 12 for long enough to sense, detect, and/or otherwise determine, for example, 3 or 4 blood pressure pulses of the patient 14 in such an additional blood pressure determination cycle. In such embodiments, the cuff 12 need not be inflated to or above the systolic pressure illustrated in FIG. 3, and in some situations in which such a procedure is used, the cuff 12 need not be inflated to or above the peak pressure illustrated in FIG. 3. Accordingly, such procedures may reduce the amount of time required to determine an accurate blood pressure of the patient 14, and may further reduce the discomfort associated with such blood pressure determinations. It is understood, however, that the width of the acceptable pulse height range 46 may be minimized in order to ensure the accuracy of such additional blood pressure determinations. For example, the upper pulse curve threshold 42 may be defined by a plurality of points having pulse height values within approximately 3% of (i.e., not more than approximately 3% greater than) the values corresponding to the points 40a, 40b on the initial pulse curve 32. Likewise, the lower pulse curve threshold 44 may be defined by a plurality of points having pulse height values within approximately 3% of (i.e., not more than approximately 3% less than) the values corresponding to the points 40a, 40b on the initial pulse curve 32. In example embodiments, such a procedure may begin upon completion of, for example, step: 228 of FIG. 2, and may be repeated every 15 minutes, every half-hour, every hour, and/or on any other desired interval during monitoring of the patient 14. Further, such pulse curve thresholds 42, 44 may be determined by the controller 20 during or after generation of the pulse curve 32 at step: 218. Alternatively, such pulse curve thresholds 42, 44 may be predetermined thresholds stored in the memory 24.

The example systems and methods of the present disclosure overcome various deficiencies of known prior art devices. For example, the system 100 is configured to determine the blood pressure of the patient 14 in less time than known systems, thereby reducing the overall evaluation time required for each patient. Additionally, since the system 100 is configured to utilize a minimum number of blood pressure pulses to determine the blood pressure, such blood pressure determinations may reduce the level of patient discomfort associated with blood pressure measurement as compared to other known systems. For example, in any of the embodiments disclosed herein, the system 100 may determine the blood pressure of the patient 14 without completely occluding the blood vessel 10.

Other embodiments of the present disclosure will be apparent to those skilled in the art from consideration of the specification and practice of the disclosure contained herein. It is intended that the specification and examples be considered as example only, with a true scope and spirit of the present disclosure being indicated by the following claims.

What is claimed is:

1. A method of determining a blood pressure of a patient, comprising:
   disposing a cuff around a limb of the patient;
   determining a plurality of pressure pulses during inflation of the cuff, wherein each pressure pulse of the plurality of pressure pulses
   comprises a profile having a maximum profile height, and
   corresponds to a different respective inflation pressure of the cuff;
   determining a pulse score associated with the plurality of pressure pulses, wherein the pulse score is determined by one or more algorithms based on the profiles of the pressure pulses and the maximum profile heights;
   determining that the pulse score is above a pulse score threshold;
   generating, in response to determining that the pulse score is above the pulse score threshold, a pulse curve based on the maximum profile heights; and
   determining the blood pressure of the patient without completely occluding a blood vessel of the patient, wherein the blood pressure is determined by the one or more algorithms based on a plurality of values corresponding to respective points on the pulse curve.

2. The method of claim 1, further comprising
   inflating the cuff toward a first target inflation pressure, wherein the plurality of pressure pulses comprises a plurality of sequential pressure pulses associated with the blood vessel of the patient.

3. The method of claim 2, wherein each maximum profile height is indicative of a maximum force exerted on the cuff during a corresponding pressure pulse of the plurality of pressure pulses, and wherein the maximum force is a result of blood flow through the limb.

4. The method of claim 2, wherein each profile is defined by values indicative of force exerted on the cuff during a corresponding pressure pulse of the plurality of pressure pulses, and wherein the force is a result of blood flow through the limb.

5. The method of claim 2, further comprising:
   comparing each maximum profile height to a pressure threshold;
   identifying a subset of the maximum profile heights having a value greater than the pressure threshold;
   matching the subset of the maximum profile heights with a stored set of profile heights; and
   continuing inflation of the cuff toward a second target inflation pressure corresponding to the stored set of profile heights.

6. The method of claim 1, wherein the blood pressure of the patient is determined during inflation of the cuff.

7. The method of claim 1, wherein the plurality of pressure pulses is determined without completely occluding the blood vessel when the cuff is inflated to inflation pressures between a systolic blood pressure of the patient and a diastolic blood pressure of the patient.

8. The method of claim 1, wherein the plurality of pressure pulses comprises a first pulse, a second pulse, and a third pulse,
the first pulse comprising a first profile defined by a first plurality of values, the first plurality of values being indicative of force exerted on a cuff during the first pulse, the first plurality of values including a first maximum profile height,
the second pulse comprising a second profile defined by a second plurality of values, the second plurality of values being indicative of force exerted on the cuff during the second pulse, the second plurality of values including a second maximum profile height,
the third pulse comprising a third profile defined by a third plurality of values, the third plurality of values being indicative of force exerted on the cuff during the third pulse, the third plurality of values including a third maximum profile height, the method further comprising:
generating a first reference curve by averaging values of the first plurality of values with corresponding values of the second plurality of values, the first reference curve being defined by a fourth plurality of values; and
generating a second reference curve by subtracting values of the third plurality of values from corresponding values of the fourth plurality of values.

9. The method of claim 8, wherein the second reference curve is defined by a fifth plurality of values, and wherein the pulse score is determined by using the fifth plurality of values and the maximum profile heights as inputs to the one or more algorithms.

10. The method of claim 1, wherein the plurality of values includes a peak pressure value, the method further comprising:
identifying a first subset of the plurality of values relative to the peak pressure value;
identifying a second subset of the plurality of values relative to the peak pressure value, the second subset of values being exclusive of the first subset of values; and
determining the blood pressure by using the first and second subsets of values, and the peak pressure value, as inputs to the one or more algorithms.

11. The method of claim 10, wherein the plurality of values includes a remainder of values exclusive of the first subset, the second subset, and the peak pressure value, and wherein the blood pressure is determined by the one or more algorithms without the remainder of values.

12. The method of claim 1, wherein the pulse curve comprises a best-fit curve derived from the maximum profile heights, and wherein the plurality of values corresponds to points on the best-fit curve, the method further comprising:
comparing the plurality of values to a stored set of values corresponding to respective points on a predetermined pulse curve; and
determining the blood pressure in response to the comparison.

13. The method of claim 1, further comprising comparing the blood pressure to a blood pressure threshold, and outputting the blood pressure in response to the comparison.

14. The method of claim 1, wherein the blood pressure comprises a systolic pressure and a diastolic pressure, the method further comprising:
comparing the systolic pressure to a first threshold;
comparing the diastolic pressure to a second threshold different from the first threshold; and
determining the blood pressure
in response to comparing at least one of the systolic pressure and the diastolic pressure, and
while an inflation pressure of the cuff if between the systolic pressure and the diastolic pressure.

15. The method of claim 1, wherein the blood pressure comprises a first blood pressure, the pulse curve comprises a first pulse curve, the plurality of values comprises a first plurality of values, and the maximum heights comprise a first plurality of maximum heights, the method further comprising:
generating a second pulse curve based on a second plurality of maximum heights different from the first plurality of maximum heights;
comparing the first plurality of values to values corresponding to points on the second pulse curve; and
outputting the first blood pressure in response to the comparing.

16. A blood pressure measurement system, comprising:
a cuff;
a sensor configured to determine a plurality of pressure pulses of a patient during inflation of the cuff and while the cuff is disposed around a limb of the patient, wherein each pressure pulse of the plurality of pressure pulses
comprises a profile having a maximum profile height, and
corresponds to a different respective inflation pressure of the cuff;
a controller in communication with the sensor, the controller configured to:
determine a pulse score associated with the plurality of pressure pulses, wherein the pulse score is determined by one or more algorithms associated with the controller based on the profiles of the pressure pulses and the maximum profile heights,
determine if the pulse score is above a pulse score threshold,
generate, in response to determining that the pulse score is above the pulse score threshold, a pulse curve based on the maximum profile heights, and
determine the blood pressure of the patient without completely occluding a blood pressure of the patient, wherein the blood pressure is determined based on a plurality of values corresponding to respective points on the pulse curve; and
a user interface in communication with the controller, the user interface configured to output the blood pressure.

17. The system of claim 16, wherein the cuff is selectively inflatable around the limb of the patient under control of the controller.

18. The system of claim 17, wherein the plurality of pressure pulses comprises at least four pressure pulses.

19. The system of claim 17, wherein:
the sensor comprises a pressure transducer;
each maximum profile height is indicative of a maximum force, sensed by the pressure transducer, exerted on the cuff during a corresponding pressure pulse of the plurality of pressure pulses; and
the maximum force is a result of blood flow through the limb.

20. The system of claim 16, further comprising a memory in communication with the controller, the memory including a stored pressure threshold and stored sets of profile heights, wherein the controller is configured to:
 compare each maximum profile height to the pressure threshold;
 identify a subset of the maximum profile heights having a value greater than the pressure threshold; and
 match the subset of the maximum profile heights with at least one set of the stored sets of profile heights.

21. The system of claim 16, further comprising a memory in communication with the controller, the memory including a stored set of values corresponding to points on a predetermined pulse curve, wherein the controller is configured to:
 compare the plurality of values to the stored set of values; and
 determine the blood pressure in response to the comparison.

22. A method of manufacturing a blood pressure measurement system, comprising:
 providing a cuff;
 providing a sensor configured to determine a plurality of pressure pulses of a patient during inflation of the cuff and while the cuff is disposed around a limb of the patient, wherein each pressure pulse of the plurality of pressure pulses
  comprises a profile having a maximum profile height, and
  corresponds to a different respective inflation pressure of the cuff; and
 operably connecting the sensor to a controller, the controller configured to:
  determine a pulse score associated with the plurality of pressure pulses, wherein the pulse score is determined based on the profiles of the pressure pulses and the maximum profile heights,
  determine that the pulse score is above a pulse score threshold,
  generate, in response to determining that the pulse score is above the pulse score threshold, a pulse curve based on the maximum profile heights,
  determine the blood pressure of the patient without completely occluding a blood vessel of the patient, wherein the blood pressure is determined based on a plurality of values corresponding to respective points on the pulse curve, and
  communicate with a user interface, the user interface configured to output the blood pressure.

23. The method of claim 22, further comprising operably connecting the cuff to the controller, the controller being configured to selectively inflate the cuff to the different respective inflation pressures, and wherein the different respective inflation pressures comprise a series of sequentially increasing pressures between a systolic pressure of the patient and a diastolic pressure of the patient.

24. The method of claim 22, further comprising communication between a memory and the controller, the memory including a stored pressure threshold and stored sets of profile heights, wherein the controller is configured to:
 compare each maximum profile height to the pressure threshold;
 identify a subset of the maximum profile heights having a value greater than the pressure threshold; and
 match the subset of the maximum profile heights with at least one set of the stored sets of profile heights.

25. The method of claim 24, wherein the memory further includes a stored set of values corresponding to points on a predetermined pulse curve, wherein the controller is configured to:
 compare the plurality of values to the stored set of values; and
 determine the blood pressure in response to the comparison.

* * * * *

UNITED STATES PATENT AND TRADEMARK OFFICE
CERTIFICATE OF CORRECTION

PATENT NO. : 9,750,419 B2  
APPLICATION NO. : 14/183074  
DATED : September 5, 2017  
INVENTOR(S) : Tyson B. Whitaker et al.

Page 1 of 1

It is certified that error appears in the above-identified patent and that said Letters Patent is hereby corrected as shown below:

On the Title Page

Column 1, Line 11, change "Buchanon" to -- Buchanan --.

Signed and Sealed this  
Second Day of January, 2018

Joseph Matal  
*Performing the Functions and Duties of the*  
*Under Secretary of Commerce for Intellectual Property and*  
*Director of the United States Patent and Trademark Office*